United States Patent
Ferrari

(10) Patent No.: US 6,869,594 B2
(45) Date of Patent: Mar. 22, 2005

(54) TRANSFER-FREE MASCARA COMPOSITION COMPRISING AT LEAST ONE VOLATILE SOLVENT AND AT LEAST ONE POLYMER

(75) Inventor: Véronique Ferrari, Maisons-Alfort (FR)

(73) Assignee: L'Oréal S.A., Paris (FR)

( * ) Notice: Subject to any disclaimer, the term of this patent is extended or adjusted under 35 U.S.C. 154(b) by 390 days.

(21) Appl. No.: 09/937,314

(22) PCT Filed: Jan. 24, 2001

(86) PCT No.: PCT/FR01/00229

§ 371 (c)(1),
(2), (4) Date: Dec. 6, 2001

(87) PCT Pub. No.: WO01/52799

PCT Pub. Date: Jul. 26, 2001

(65) Prior Publication Data

US 2004/0156813 A2 Aug. 12, 2004

(30) Foreign Application Priority Data

Jan. 24, 2000 (FR) .............................. 00 00920

(51) Int. Cl.$^7$ ................................................ A61K 7/48
(52) U.S. Cl. ...................................... 424/10.7; 424/407
(58) Field of Search ................................ 424/707, 401, 424/63, 64

(56) References Cited

U.S. PATENT DOCUMENTS

| | | | |
|---|---|---|---|
| 2,379,413 A | 7/1945 | Bradley | |
| 2,450,940 A | 10/1948 | Cowan et al. | |
| 2,662,068 A | 12/1953 | Floyd | |
| 2,663,649 A | 12/1953 | Winkler | |
| 2,890,097 A | 6/1959 | Coe | |
| 2,962,461 A | 11/1960 | Toussaint et al. | |
| 3,086,914 A | 4/1963 | Soloway ..................... | 167/85 |
| 3,141,787 A | 7/1964 | Goetze et al. | |
| 3,148,125 A | 9/1964 | Strianse et al. | |
| 3,156,572 A | 11/1964 | Carlick et al. | |
| 3,255,082 A | 6/1966 | Barton | |
| 3,341,465 A | 9/1967 | Kaufman et al. | |
| 3,412,115 A | 11/1968 | Floyd et al. | |
| 3,615,289 A | 10/1971 | Felton | |
| 3,645,705 A | 2/1972 | Miller et al. | |

(List continued on next page.)

FOREIGN PATENT DOCUMENTS

| | | |
|---|---|---|
| CA | 2003346 | 5/1990 |
| CA | 1319306 | 6/1993 |
| DE | 38 39 136 A1 | 5/1990 |
| EP | 0 370 470 B1 | 5/1990 |
| EP | 0 444 633 A2 | 9/1991 |
| EP | 0 295 886 B1 | 1/1992 |
| EP | 0 374 332 B1 | 1/1993 |
| EP | 0 623 670 A2 | 11/1994 |
| EP | 0 628 582 B1 | 12/1994 |
| EP | 0 412 710 B1 | 7/1995 |
| EP | 0 673 642 B1 | 9/1995 |
| EP | 0 708 114 A1 | 4/1996 |
| EP | 0 775 483 | 5/1997 |
| EP | 0 797 976 A2 | 10/1997 |
| EP | 0 820 764 | 1/1998 |

(List continued on next page.)

OTHER PUBLICATIONS

English language Derwent abstract of JP 02/200612.
English language Derwent abstract of JP 09/255560.
English language Derwent abstract of JP 10/007527.
English language Derwent abstract of JP 10/212213.
English language Derwent abstract of EP 0 923 928 A1.
English language Derwent abstract of EP 0 925 780 A1.
English language Derwent abstract of EP 0 943 340 A1.
English language Derwent abstract of EP 1 608 856 A1.
English language Derwent abstract of FR 2 796 270.
English language Derwent abstract of FR 2 796 271.
English language Derwent abstract of FR 2 796 276.
English language Derwent abstract of FR 2 811 552 A1.
English language Derwent abstract of FR 2 816 506.
English language Derwent abstract of FR 2 232 303.
English language Derwent abstract of JP 53043577.

(List continued on next page.)

*Primary Examiner*—Jyothsna Venkat
(74) *Attorney, Agent, or Firm*—Finnegan, Henderson, Farabow, Garrett, & Dunner, LLP

(57) ABSTRACT

The invention relates to a physiologically acceptable, in particular mascara, cosmetic composition comprising at least one volatile solvent and at least one polymer chosen from polymers of following formula (I):

$$R^1-O-\underset{\underset{O}{\|}}{C}-R^2-\underset{\underset{O}{\|}}{C}-N-R^3-\underset{n}{\overset{R^4}{N}}-\underset{\underset{O}{\|}}{C}-R^2-\underset{\underset{O}{\|}}{C}-O-R^1 \quad (I)$$

in which n denotes a number of amide units, such that the number of ester groups represents from 10% to 50% of the total number of ester and amide groups: $R^1$ is in each case, independently an alkyl or alkenyl group having at least 4 carbon atoms; $R^2$ independently represents in each case a $C_4$ to $C_{42}$ hydrocarbonaceous group, provided that 50% of the $R^2$ groups represent a $C_{30}$ to $C_{42}$ hydrocarbonaceous group; $R^3$ independently represents, in each case, an organic group provided with at least 2 carbon atoms, with hydrogen atoms and optionally with one or more oxygen or nitrogen atoms; and $R^4$ independently represents, in each case, a hydrogen atom a $C_1$ to $C_{10}$ alkyl group or a direct bond to $R^3$ or another $R^4$, so that the nitrogen atom to which both $R^3$ and $R^4$ are bonded forms part of a heterocyclic structure defined by $R^4-N-R^3$ with at least 50% of the $R^4$ groups representing a hydrogen atom.

2 Claims, No Drawings

U.S. PATENT DOCUMENTS

| | | |
|---|---|---|
| 3,778,394 A | 12/1973 | Lovald et al. |
| 3,819,342 A | 6/1974 | Gunderman et al. |
| 3,857,960 A | 12/1974 | Mackles |
| 3,926,655 A | 12/1975 | Miles |
| 3,937,811 A | 2/1976 | Papantoniou et al. |
| 3,969,087 A | 7/1976 | Saito et al. |
| 4,049,792 A | 9/1977 | Elsnau |
| 4,051,159 A | 9/1977 | Tsoucalas et al. |
| 4,062,819 A | 12/1977 | Mains et al. |
| RE29,871 E | 12/1978 | Papantoniou et al. |
| 4,128,436 A | 12/1978 | O'Hara et al. |
| 4,137,306 A | 1/1979 | Rubino et al. |
| 4,150,002 A | 4/1979 | Drawert et al. |
| 4,275,054 A | 6/1981 | Sebag et al. |
| 4,275,055 A | 6/1981 | Nachtigal et al. ............. 424/70 |
| 4,278,658 A | 7/1981 | Hooper et al. |
| 4,279,658 A | 7/1981 | Harvey et al. |
| 4,337,298 A | 6/1982 | Karim et al. |
| 4,341,671 A | 7/1982 | Bolze et al. |
| 4,376,194 A | 3/1983 | Tanaka et al. |
| 4,387,090 A | 6/1983 | Bolich, Jr. ................. 424/70 |
| 4,438,240 A | 3/1984 | Tanaka et al. |
| 4,466,936 A | 8/1984 | Schapel |
| 4,536,405 A | 8/1985 | Nara et al. |
| 4,552,693 A | 11/1985 | Hussain et al. ............. 252/522 |
| 4,571,267 A | 2/1986 | Drawert et al. |
| 4,655,836 A | 4/1987 | Drawert et al. |
| 4,663,428 A | 5/1987 | Okitu et al. |
| 4,699,779 A | 10/1987 | Palinczar |
| 4,712,571 A | 12/1987 | Remz et al. |
| 4,769,285 A | 9/1988 | Rasmussen |
| 4,806,338 A | 2/1989 | Smith .......................... 424/47 |
| 4,806,345 A | 2/1989 | Bhattacharyya ............. 424/70 |
| 4,820,765 A | 4/1989 | Whyzmuzis |
| 4,871,536 A | 10/1989 | Arraudeau et al. ........... 424/59 |
| 4,937,069 A | 6/1990 | Shin |
| 4,952,245 A | 8/1990 | Iwano et al. |
| 5,069,897 A | 12/1991 | Orr .............................. 424/66 |
| 5,102,656 A | 4/1992 | Kasat |
| 5,186,318 A | 2/1993 | Oestreich et al. ............. 206/37 |
| 5,223,559 A | 6/1993 | Arraudeau et al. |
| 5,272,241 A | 12/1993 | Lucarelli et al. .............. 528/15 |
| 5,302,398 A | 4/1994 | Egidio et al. |
| 5,342,894 A | 8/1994 | Robeson et al. |
| 5,362,482 A | 11/1994 | Yoneyama et al. |
| 5,372,852 A | 12/1994 | Titterington et al. |
| 5,389,363 A | 2/1995 | Snyder et al. |
| 5,472,686 A | 12/1995 | Tsubaki et al. |
| 5,500,209 A | 3/1996 | Mendolia et al. |
| 5,505,937 A | 4/1996 | Castrogiovanni et al. |
| 5,510,452 A | 4/1996 | Santhanam ................. 528/291 |
| 5,536,871 A | 7/1996 | Santhanam ................. 560/196 |
| 5,538,718 A | 7/1996 | Aul et al. |
| 5,538,793 A | 7/1996 | Inokuchi et al. |
| 5,540,853 A | 7/1996 | Trinh et al. .................. 510/101 |
| 5,603,925 A | 2/1997 | Ross et al. .................... 424/65 |
| 5,610,199 A | 3/1997 | Cohen et al. |
| 5,612,043 A | 3/1997 | Deprez et al. |
| 5,616,331 A | 4/1997 | Allard et al. |
| 5,618,523 A | 4/1997 | Zysman et al. |
| 5,620,693 A | 4/1997 | Piot et al. |
| 5,645,632 A | 7/1997 | Pavlin |
| 5,667,770 A | 9/1997 | Szweda et al. ............... 424/64 |
| 5,679,357 A | 10/1997 | Dubief et al. ............... 424/401 |
| 5,683,817 A | 11/1997 | Kenmochi |
| 5,719,255 A | 2/1998 | Heucher et al. |
| 5,747,625 A | 5/1998 | Furukawa et al. |
| 5,750,125 A | 5/1998 | Lahanas et al. |
| 5,750,127 A | 5/1998 | Rokitowski |
| 5,750,489 A | 5/1998 | Garcia et al. |
| 5,780,517 A | 7/1998 | Cohen et al. |
| 5,783,657 A | 7/1998 | Pavlin et al. |
| 5,800,816 A | 9/1998 | Brieva et al. ................. 424/63 |
| 5,807,968 A | 9/1998 | Heinrich et al. |
| 5,830,483 A | 11/1998 | Seidel et al. |
| 5,837,223 A | 11/1998 | Barone et al. |
| 5,849,275 A | 12/1998 | Calello et al. |
| 5,849,278 A | 12/1998 | Piot et al. |
| 5,849,333 A | 12/1998 | Nordhauser et al. |
| 5,851,517 A | 12/1998 | Mougin et al. |
| 5,857,903 A | 1/1999 | Ramspeck et al. |
| 5,858,338 A | 1/1999 | Piot et al. |
| 5,866,149 A | 2/1999 | Piot et al. |
| 5,871,764 A | 2/1999 | Diaz et al. |
| 5,874,069 A | 2/1999 | Mendolia et al. ............. 424/65 |
| 5,882,363 A | 3/1999 | Spaulding et al. |
| 5,891,424 A | 4/1999 | Bretzler et al. |
| 5,897,869 A | 4/1999 | Roulier et al. ............... 424/401 |
| 5,902,592 A | 5/1999 | Bara et al. |
| 5,908,631 A | 6/1999 | Arnaud et al. |
| 5,911,974 A | 6/1999 | Brieva et al. ................. 424/64 |
| 5,919,441 A | 7/1999 | Mendolia et al. ......... 424/78.08 |
| 5,925,337 A | 7/1999 | Arraudeau et al. |
| 5,945,095 A | 8/1999 | Mougin et al. |
| 5,945,112 A | 8/1999 | Flynn et al. |
| 5,959,009 A | 9/1999 | Konik et al. ................. 524/261 |
| 5,961,998 A | 10/1999 | Arnaud et al. |
| 5,965,112 A | 10/1999 | Brieva et al. ................. 424/64 |
| 5,972,354 A | 10/1999 | de la Poterie et al. |
| 5,972,359 A | 10/1999 | Sine et al. |
| 5,976,514 A | 11/1999 | Guskey et al. |
| 5,981,680 A | 11/1999 | Petroff et al. |
| 5,985,298 A | 11/1999 | Brieva et al. |
| 5,998,570 A | 12/1999 | Pavlin et al. |
| 6,004,567 A | 12/1999 | Marchi-Lemann et al. |
| 6,007,799 A | 12/1999 | Lee et al. |
| 6,019,962 A | 2/2000 | Rabe et al. |
| 6,036,947 A | 3/2000 | Barone et al. |
| 6,045,823 A | 4/2000 | Vollhardt et al. |
| 6,051,216 A | 4/2000 | Barr et al. ................. 424/78.35 |
| 6,054,517 A | 4/2000 | Spaulding et al. |
| 6,060,072 A | 5/2000 | Konik et al. ................. 424/401 |
| 6,063,398 A | 5/2000 | Gueret |
| 6,074,654 A | 6/2000 | Drechsler et al. ........... 424/401 |
| 6,103,249 A | 8/2000 | Roulier et al. ............... 424/401 |
| 6,106,820 A | 8/2000 | Morrissey et al. |
| 6,111,055 A | 8/2000 | Berger et al. |
| 6,156,325 A | 12/2000 | Farer et al. ................. 424/401 |
| 6,156,804 A | 12/2000 | Chevalier et al. |
| 6,165,454 A | 12/2000 | Patel et al. |
| 6,165,971 A | 12/2000 | Oppenlander et al. |
| 6,177,523 B1 | 1/2001 | Reich et al. ................. 525/459 |
| 6,180,117 B1 | 1/2001 | Berthiaume et al. |
| 6,180,123 B1 | 1/2001 | Mondet et al. |
| 6,190,673 B1 | 2/2001 | Guskey et al. ............... 424/401 |
| 6,197,100 B1 | 3/2001 | Melbouci |
| 6,203,780 B1 | 3/2001 | Arnaud et al. |
| 6,203,807 B1 | 3/2001 | Lemann |
| 6,214,329 B1 * | 4/2001 | Brieva et al. ............... 424/70.7 |
| 6,221,389 B1 | 4/2001 | Cannell et al. |
| 6,242,509 B1 | 6/2001 | Berger et al. |
| 6,251,375 B1 | 6/2001 | Bara |
| 6,251,409 B1 | 6/2001 | Hegyi et al. |
| 6,254,876 B1 | 7/2001 | de la Poterie et al. |
| 6,254,877 B1 | 7/2001 | De La Poterie et al. |
| 6,264,933 B1 | 7/2001 | Bodelin et al. |
| 6,268,466 B1 | 7/2001 | MacQueen et al. |
| 6,280,846 B1 | 8/2001 | Darby et al. |
| 6,287,552 B1 | 9/2001 | Tournilhac et al. |
| 6,325,994 B1 | 12/2001 | Collin et al. |
| 6,348,563 B1 | 2/2002 | Fukuda et al. |

| | | |
|---|---|---|
| 6,372,235 B1 | 4/2002 | Livoreil et al. |
| 6,376,078 B1 | 4/2002 | Inokuchi |
| 6,383,502 B1 | 5/2002 | Dunshee et al. |
| 6,399,081 B1 | 6/2002 | Nakanishi et al. |
| 6,402,408 B1 | 6/2002 | Ferrari |
| 6,423,306 B2 | 7/2002 | Caes et al. |
| 6,423,324 B1 | 7/2002 | Murphy et al. |
| 6,432,391 B1 | 8/2002 | Bara |
| 6,469,131 B2 | 10/2002 | Lawson et al. |
| 6,475,500 B2 | 11/2002 | Vatter et al. |
| 6,479,686 B2 | 11/2002 | Nakanishi et al. |
| 6,482,400 B1 | 11/2002 | Collin |
| 6,491,931 B1 | 12/2002 | Collin |
| 6,497,861 B1 | 12/2002 | Wang et al. |
| 2001/0014312 A1 | 8/2001 | Nakanishi et al. |
| 2002/0058053 A1 | 5/2002 | Nakanishi et al. |
| 2002/0081323 A1 | 6/2002 | Nakanishi et al. |
| 2002/0102225 A1 | 8/2002 | Hess et al. |
| 2002/0114771 A1 | 8/2002 | Nakanishi |
| 2002/0119171 A1 | 8/2002 | Gruning et al. |
| 2002/0131947 A1 | 9/2002 | Nakanishi |
| 2002/0141958 A1 | 10/2002 | Maio et al. |
| 2002/0150602 A1 | 10/2002 | Livoreil et al. |
| 2002/0159964 A1 | 10/2002 | Nakanishi et al. |
| 2003/0044367 A1 | 3/2003 | Simon et al. |

FOREIGN PATENT DOCUMENTS

| | | |
|---|---|---|
| EP | 0 847 752 | 6/1998 |
| EP | 0 877 063 B1 | 11/1998 |
| EP | 0 879 592 A2 | 11/1998 |
| EP | 0 928 608 A2 | 7/1999 |
| EP | 0 958 804 A2 | 11/1999 |
| EP | 0 958 805 A2 | 11/1999 |
| EP | 1 062 944 A1 | 12/2000 |
| EP | 1 062 959 A1 | 12/2000 |
| EP | 1 095 959 A2 | 5/2001 |
| EP | 1 213 011 A1 | 6/2002 |
| EP | 1 213 316 A2 | 6/2002 |
| FR | 1 529 329 | 5/1968 |
| FR | 2 819 402 | 7/2002 |
| GB | 1 117 129 | 6/1968 |
| GB | 1 194 901 | 6/1970 |
| GB | 1 194 902 | 6/1970 |
| GB | 1 220 069 | 1/1971 |
| GB | 1 273 004 | 5/1972 |
| GB | 1 444 204 | 7/1976 |
| GB | 2 014 852 | 9/1979 |
| GB | 2 021 411 A | 12/1979 |
| GB | 2 147 305 A | 5/1985 |
| GB | 2 196 978 A | 5/1988 |
| JP | 62-61911 | 3/1987 |
| WO | WO 86/04916 | 5/1986 |
| WO | WO 93/21763 | 11/1993 |
| WO | WO 93/23008 | 11/1993 |
| WO | WO 94/18261 | 8/1994 |
| WO | WO 95/24887 | 9/1995 |
| WO | WO 96/15761 | 5/1996 |
| WO | WO 96/40044 | 12/1996 |
| WO | WO 97/17057 | 5/1997 |
| WO | WO 87/03783 | 7/1997 |
| WO | WO 97/36573 | 10/1997 |
| WO | WO 98/17243 | 4/1998 |
| WO | WO 98/17705 | 4/1998 |
| WO | WO 98/22078 | 5/1998 |
| WO | WO 98/27162 | 6/1998 |
| WO | WO 98/42298 | 10/1998 |
| WO | WO 98/47470 | 10/1998 |
| WO | WO 98/52534 | 11/1998 |
| WO | WO 98/58623 | 12/1998 |
| WO | WO 99/24002 | 5/1999 |
| WO | WO 00/40216 | 7/2000 |
| WO | WO 00/61080 | 10/2000 |
| WO | WO 00/61081 | 10/2000 |
| WO | WO 00/7519 A2 | 12/2000 |
| WO | WO 01/51020 A1 | 7/2001 |
| WO | WO 01/52799 A1 | 7/2001 |
| WO | WO 01/97758 A2 | 12/2001 |
| WO | WO 01/97773 A1 | 12/2001 |
| WO | WO 02/03932 A2 | 1/2002 |
| WO | WO 02/03935 A2 | 1/2002 |
| WO | WO 02/03950 A2 | 1/2002 |
| WO | WO 02/03951 A1 | 1/2002 |
| WO | WO 02/47608 A2 | 6/2002 |
| WO | WO 02/47619 A2 | 6/2002 |
| WO | WO 02/47620 A2 | 6/2002 |
| WO | WO 02/47622 A2 | 6/2002 |
| WO | WO 02/47629 A1 | 6/2002 |
| WO | WO 02/47630 A1 | 6/2002 |
| WO | WO 02/47658 A2 | 6/2002 |
| WO | WO 02/49583 A1 | 6/2002 |
| WO | WO 02/49601 A1 | 6/2002 |
| WO | WO 02/055030 A2 | 7/2002 |
| WO | WO 02/056847 A1 | 7/2002 |
| WO | WO 02/056848 A1 | 7/2002 |
| WO | WO 02/092047 A1 | 11/2002 |
| WO | WO 02/092663 A1 | 11/2002 |
| WO | WO 02/102322 A2 | 12/2002 |

OTHER PUBLICATIONS

English language Derwent abstract of JP 56123909.
English language Derwent abstract of JP 61065809.
English language Derwent abstract of FR 2 674 126.
English language Derwent abstract of JP 04346909.
English language Derwent abstract of EP 0 557 196 A1.
English language Derwent abstract of EP 0 609 132.
English language Derwent abstract of abstract of JP 7267827.
English language Derwent abstract of JP 8225316.
English language Derwent abstract of EP 0 749 746 A1.
English language Derwent abstract of EP 0 749 747 A1.
English language Derwent abstract of EP 0 775 483 A1.
English language Derwent abstract of EP 0 879 592 A2.
English language Derwent abstract of EP 0 887 073 A1.
English language Derwent abstract of JP 11106216.
English language Derwent abstract of EP 0 959 066 A2.
English language Derwent abstract of EP 0 930 058 B1.
English language Derwent abstract of EP 0 930 060 A1.
English language Derwent abstract of EP 0 958 811 A1.
English language Derwent abstract of EP 0 959 091 A1.
English language Derwent abstract of EP 0 976 390 A1.
English language Derwent abstract of EP 0 984 025 A2.
English language Derwent abstract of FR 2 785 179.
English language Derwent abstract of EP 1 002 514.
English language Derwent abstract of EP 1 031 342 A1.
English language Derwent abstract of EP 1 048 282 A1.
English language Derwent abstract of EP 1 053 742.
English language Derwent abstract of EP 1 064 919.
English language Derwent abstract of EP 1 064 920.
English language Derwent abstract of EP 1 066 814.
English language Derwent abstract of EP 1 068 854 A1.
English language Derwent abstract of EP 1 068 855 A1.
English language Derwent abstract of EP 1 068 856 A1.
English language Derwent abstract of EP 1 086 945 A1.
English language Derwent abstract of EP 1 090 627 B1.
English language Derwent abstract of FR 2 802 806.
English language Derwent abstract of EP 1 114 636 A1.
English language Derwent abstract of WO 02/055031 A1.
English language Derwent abstract of FR 2 819 402.

English language Derwent abstract of WO 02/056845 A1.
English language Derwent abstract of JP 9295922 A.
English language Derwent abstract of JP 7179795A.
English language Derwent abstract of JP 3014683.
English language Derwent abstract of JP 2216279.
English language Derwent abstract of JP 2127568.
English language Derwent abstract of JP 10259344.
English language Derwent abstract of DE 3839136.
English language Derwent abstract of DE 197 07 309.
English language Derwent abstract of DE 197 50 246.
English language Derwent abstract of EP 0 374332 A1.
English language Derwent abstract of JP 56166276A.
English language Derwent abstract of EP 0 749 748.
English language Derwent abstract of De 42 34 886.
English language Derwent abstract of DE 42 08 297.
English language Derwent abstract of DE 38 43 892.
English language Derwent abstract of DE 195 43 988.
English language Derwent abstract of DE 199 51 010.
English language Derwent abstract of EP 0 958 085 B1.
English language Derwent abstract of JP 9020631.
English language Derwent abstract of JP 10/120903.
English language Derwent abstract of JP 1135228.
English language Derwent abstract of JP 11335242.
English language Derwent abstract of JP 11335254.
English language Derwent abstract of JP 2000038314 A.
English language Derwent abstract of JP 2000038316 A.
English language Derwent abstract of JP 2000038317 A.
English language Derwent abstract of JP 2000038321 A.
English language Derwent abstract of JP 2000086427 A.
English language Derwent abstract of JP 2000086429 A.
English language Derwent abstract of JP 2000086438 A.
Certified English translation of FR 1 529 329.
Kirk–Othmer, "Encyclopedia of Chemical Technology", Third Edition, vol. 22, John Wiley & Sons, 1983, pp. 332–432.
Charles M. Hansen, "The Three Dimensional Solubility Parameter—Key to Paint Component Affinities: I. Solvents, Plasticizers, Polymers, and Resins," Journal of Paint Technology, vol. 39, No. 505, Feb. 1967, pp. 104–117.
Milan Jokić et al., A Novel Type of Small Organic Gelators: Bis(Amino Acid) Oxalyl Amides, 1995 J. Chem. Soc., Chem. Commun., 1723–1724.
Yasuda et al., Novel Low–molecular–weight Organic Gels: N,N', N"–Tristearyltrimesamide/Organic Solvent System, Chemistry Letters, pp. 575–576, 1996, the month of publication is not available.
Kenji Hanabusa et al., Prominent Gelation and Chiral Aggregation of Alkylamides Derived from trans–1,2–Diaminocyclohexane, Angew. Chem. Int. Ed. Engl. 1996, 35, No. 17, 1949–1951.
Toshimi Shimizu et al., Stereochemical Effect of Even–Odd Connecting Links on Supramolecular Assemblies Made of 1–Glucosamide Bolaamphiphiles, J. Am Chem. Soc. 1997, 119, 2812–2818.
P. Terech, "Low–Molecular Weight Organogelators," in Specialist Surfactants, ch. 8, pp. 208–268 (I.D. Robb, ed., 1997).
Kenji Hanabusa et al., Terephthaloyl Derivatives as New Gelators; Excellent Gelation Ability and Remarkable Increase of Gel Strength by Adding Polymers, 1999 Chemistry Letters 767.
Xuzhong Luo et al., Self–assembled organogels formed by monoalkyl derivatives of oxamide, 2000 Chem. Commun. 2091–92.

Kenji Hanabusa et al., Easy Preparation and Gelation of New Gelator Based on L–Lysine, 2000 Chem. Letters, 1070.
Bush Boake Allen, Inc., Uniclear Formulations, dated Oct. 13, 1998.
U.S. Appl. No. 2002/0114773 A1, filed Aug. 22, 2002.
U.S. Appl. No. 2002/0122781 A1, filed Sep. 5, 2002.
U.S. Appl. No. 2002/0120036 A1, filed Aug. 29, 2002.
U.S. Appl. No. 2002/0107314 A1, filed Aug. 8, 2002.
U.S. Appl. No. 2002/0111330 A1, filed Aug. 15, 2002.
U.S. Appl. No. 2001/0031280 A1, filed Oct. 18, 2001.
U.S. Appl. No. 2002/0044918 A1, filed Apr. 18, 2002.
U.S. Appl. No. 2003/0012764 A1, filed Jan. 16, 2003.
U.S. Appl. No. 2002/0189030 A1, filed Dec. 19, 2002.
U.S. Appl. No. 2002/0168335 A1, filed Nov. 14, 2002.
U.S. Appl. No. 2002/0192168 A1, filed Dec. 19, 2002.
U.S. Appl. No. 2002/0172696 A1, filed Nov. 21, 2002.
U.S. Appl. No. 2003/0026772 A1, filed Feb. 6, 2003.
U.S. Appl. No. 2003/0044367 A1, filed Mar. 6, 2003.
International Search Report in PCT/US 01/47459 (Atty. Docket No. 5725.0594–0304), dated Feb. 6, 2003.
International Search Report in PCT/US 01/47496 (Atty. Docket No. 5725.0809–0304), dated Feb. 26, 2003.
International Search Report in PCT/US 01/47499 (Atty. Docket No. 5725.0595–0304), dated Aug. 8, 2002.
International Search Report in PCT/US 01/47454 (Atty. Docket No. 5725.0806–0304), dated Aug. 29, 2002.
Partial International Search Report in PCT/US 01/47497 (Atty. Docket No. 5725.0808–0304), dated Aug. 30, 2002.
International Search Report in PCT/US01/47497 (Atty. Docket No. 5725.0808–0304), dated Dec. 2, 2002.
French Search Report in FR 9909176 (priority document for Atty. Docket No. 5725.0659), dated Mar. 23, 2000.
French Search Report in FR 9909177 (priority document for Atty. Docket No. 5725.0656).
French Search Report in FR 9916588 (priority document for Atty. Docket No. 5725.0832), dated Oct. 16, 2000.
French Search Report in FR 0001004 (priority document for Atty. Docket No. 5725.0832), dated Nov. 10, 2000.
French Search Report in FR 0000920 (priority document for PCT/FR01/002299, which is the priority document for Atty. Docket No. 5725.0932), dated Nov. 10, 2000.
Internat
French Search Report in FR 0008084 (priority document for Atty. Docket No. 5725.1187), dated Mar. 28, 2001.
International Search Report in PCT/FR01/01958 (priority document for Atty. Docket No. 5725.1187), dated Oct. 26, 2001.
French Search Report in FR 0008913 (priority document for Atty. Docket No. 5725.0920), dated Mar. 28, 2001.
French Search Report in FR 0016161 (priority document for Atty. Docket No. 5725.1003), dated Sep. 6, 2001.
International Search Report in PCT/FR01/03940 (priority document for FR 0016161, which is the priority document for Atty. Docket No. 5725.1003), dated Mar. 13, 2002.
French Search Report in FR 0016163 (priority document for Atty. Docket No. 5725.1005), dated Aug. 1, 2001.
International Search Report in PCT/FR01/03945 (priority document for FR 0016163, which is the priority document for Atty. Docket No. 5725.1003), dated May. 31, 2002.
International Search Report in PCT/FR01/03939 (priority document for FR 0016164, which is the priority document for Atty. Docket No. 5725.1003), dated Apr. 15, 2002.
French Search Report in FR 0016164 (priority document for Atty. Docket No. 5725.1004), dated Sep. 6, 2001.

International Search Report in PCT/FR01/03937 (priority document for Atty. Docket No. 6028.0018), dated Apr. 23, 2002.
French Search Report in FR 0016180 (priority document for Atty. Docket No. 6028.0019), dated Oct. 16, 2001.
International Search Report in PCT/FR01/03938 (priority document for Atty. Docket No. 6028.0019), dated Jun. 10, 2002.
International Search Report in PCT/IB01/02780 (Atty. Docket No. 5725.0819–01304), dated Apr. 10, 2002.
International Search Report in PCT/US00/33596 (Atty. Docket No. 5727.0795–0304), dated Aug. 8, 2001.
International Search Report in PCT/IB00/02000 (Atty. Docket No. 5727.0816–00304), dated Aug. 8, 2001.
International Search Report in PCT/IB10/02833 (Atty. Docket No. 5727.0816–01304), dated May 24, 2002.
International Search Report in PCT/IB00/02006 (Atty. Docket No. 5727.0817–00304), dated Aug. 8, 2001.
International Search Report in PCT/IB01/02840 (Atty. Docket No. 5727.0817–01304), dated Jun. 11, 2002.
International Search Report in PCT/IB01/02820 dated May 27, 2002.
International Search Report in PCT/IB00/02002, dated Sep. 4, 2001.
International Search Report in PCT/IB01/02786, dated Oct. 2, 2002).
French Search Report in FR 0100479, dated Sep. 17, 2001.
International Search Report in PCT/FR02/00129, dated Jun. 14, 2002.
French Search Report in FR 0100623 (priority document for Atty. Docket No. 5725.1018), dated Oct. 9, 2001.
International Search Report in PCT/FR02/00144 (priority document for FR 0100479, which is the priority document for Atty.Docket No. 5725.1018), dated Jun. 14, 2002.
French Search Report in FR 0100620, dated Nov. 6, 2001.
International Search Report in PCT/FR02/00194, dated May 12, 2002.
French Search Report in FR 0114529, dated Aug. 26, 2002.
French Search Report in FR 0114530, dated Aug. 26, 2002.
International Search Report in PCT/FR01/03726, dated Apr. 9, 2002.
U.S. Appl. No. 2001/0014313, A1, filed Aug. 16, 2001.
U.S. Appl. No. 2001/0028887, A1, filed Oct. 11, 2001.
U.S. Appl. No. 2001/0033846, A1, filed Oct. 25, 2001.
Hanabusa et al., Easy Preparation and Prominent Gelation of New Gelator Based on L–Lysine, Chemistry Letters 1070–71 (2000).

Handbook of Cosmetic Science and Technology, p. 19 (Elsevier Advanced Technology 1st ed. 1994).
U.S. Appl. No. 2001/0014312 A1, filed Aug. 16, 2001, Nakanishi et al.
U.S. Appl. No. 2002/0058053 A1, filed May 16, 2002, Nakanishi et al.
U.S. Appl. No. 2002/0081323 A1, filed Jun. 27, 2002, Nakanishi et al.
U.S. Appl. No. 2002/0102225 A1, filed Aug. 1, 2002, Hess et al.
U.S. Appl. No. 2002/0114771 A1, filed Aug. 22, 2002, Nakanishi.
U.S. Appl. No. 2002/0131947 A1, filed Sep. 19, 2002, Nakanishi.
U.S. Appl. No. 2002/0141958 A1, filed Oct. 3, 2002, Mair et al.
U.S. Appl. No. 2002/0159964 A1, filed Oct. 31, 2002 Nakanishi et al.
Estee Lauder MagnaScopic® Maximum Volume mascara product packaging, believed to have first been sold in 2003.
Origins Full Story™ Lush lash mascara product packaging, believed to have first been sold in 2003.
English language Derwent Abstract of EP 0 820 764, Jan. 28, 1998.
English language Derwent Abstract of EP 0 847,752, Jun. 17, 1998.
English language Derwent Abstract of JP 62–61911, Mar. 18, 1987.
English language Derwent Abstract of EP 0 169 997 B.
English language Derwent Abstract of FR 2 796 272.
English language Derwent Abstract of FR 2 796 273.
English language Derwent Abstract of FR 2 804 071.
English language Derwent Abstract of FR 2 804 018.
English language Derwent Abstract of FR 2 810 562.
English language Derwent Abstract of FR 2 811 225.
English language Derwent Abstract of FR 2 817 739.
English language Derwent Abstract of FR 2 817 740.
English language Derwent Abstract of FR 2 817 743.
English language Derwent Abstract of FR 2 819 399.
English language Derwent Abstract of FR 2 819 400.

* cited by examiner

TRANSFER-FREE MASCARA COMPOSITION COMPRISING AT LEAST ONE VOLATILE SOLVENT AND AT LEAST ONE POLYMER

The present invention relates to a composition for caring for and/or treating and/or making up the skin, including the scalp, and/or lips of human beings, comprising a liquid fatty phase including a volatile solvent, structured by a specific polymer. This composition is provided in particular in the form of a make-up stick and more specifically a stick of lipstick, the application of which results in a notable glossy and transfer-free layer.

In cosmetic or dermatological products, it is commonplace to find a structured, namely gelled and/or stiffened, liquid fatty phase; this is in particular the case in solid compositions, such as deodorants, lip balms, lipsticks, concealers and cast foundations. This structuring is obtained using waxes and/or fillers. Unfortunately, these waxes and fillers have a tendency to render the composition matt, which is not always desirable, in particular for a lipstick; this is because women are always looking for a lipstick in the form of a stick depositing an increasingly glossy film.

The term "liquid fatty phase" is understood to mean, within the meaning of the invention, a fatty phase which is liquid at ambient temperature (25° C.) and at atmospheric pressure (760 mm of Hg) and which is composed of one or more fatty substances which are liquid at ambient temperature, also known as oils, and which are generally compatible with one another.

The structuring of the liquid fatty phase makes it possible in particular to limit its exudation from solid compositions, in particular in hot and humid regions, and furthermore to limit, after deposition on the skin or lips, the migration of this phase into the wrinkles and fine lines, which is particularly desired for a lipstick or an eyeshadow. This is because significant migration of the liquid fatty phase, in particular when it is laden with coloring materials, leads to an unsightly effect around the lips and eyes, particularly accentuating the wrinkles and fine lines. This migration is often mentioned by women as a major failing of conventional lipsticks or eyeshadows.

The gloss is essentially related to the nature of the liquid fatty phase. Thus, it is possible to reduce the level of waxes and fillers in the composition in order to increase the gloss of a lipstick but then the migration of the liquid fatty phase increases. In other words, the levels of waxes and of fillers necessary for the preparation of a stick of suitable hardness which does not exude at ambient temperature are a brake on the gloss of the layer.

The Applicant has found that the loss in gloss of a stick comprising waxes is related to the anisotropic crystalline structure of these compounds. The Applicant has thus envisaged the manufacture of a stick while reducing the level of wax and/or fillers.

Furthermore, the majority of make-up or care compositions, when they are applied to the skin, eyelashes or lips, exhibit the disadvantage of transferring, that is to say of being at least partly deposited and leaving traces on certain substrates with which they may be brought into contact, in particular a glass, a cup, a cigarette, an item of clothing or the skin. This results in mediocre persistence of the applied film, requiring the regular renewal of the application of the composition, in particular a foundation or lipstick composition. In point of fact, it is the wish of users today to beautify their faces, including the lips, and their bodies while spending the least possible time doing so.

Furthermore, the appearance of these unacceptable traces, in particular on blouse collars, can dissuade some women from using this type of make up.

For some years, cosmetic scientists have been interested in lipstick compositions and more recently in foundation compositions which are "transfer-free". Thus, the company Shiseido has envisaged, in its Patent Application JP-A-61-65809, "transfer-free" liquid lipstick compositions comprising a siloxysilicate resin (with a three-dimensional network), a volatile silicone oil with a cyclic silicone chain and pulverulent fillers. Likewise, the company Noevier has disclosed, in the document JP-A-62-61911, "transfer-free" lipstick, eyeliner and foundation compositions comprising one or more volatile silicones in combination with one or more hydrocarbonaceous waxes.

These compositions, although exhibiting improved "transfer-free" properties, have the disadvantage of leaving on the lips, after evaporation of the silicone oils, a film which becomes uncomfortable over time (feeling of dryness and of tautness), dissuading a number of women from this type of lipstick. In addition, the film deposited is matt.

Furthermore, the company Procter & Gamble has envisaged, in its Patent Application WO-A-96/40044, lipstick compositions exhibiting "transfer-free" properties comprising a volatile oil and a non-volatile oil of perfluoropolyether type which are incompatible. Furthermore, this application discloses the improvement in the gloss by virtue of the prior dispersion of an oily phase of a matrix and the ability of this oily phase to separate during the application of the product to the support and to migrate to the surface of the film thus deposited.

This system has the disadvantage of requiring a good dispersion of the oily phase in the matrix and can lead to problems of stability of the product related to the necessary poor compatibility of the oily phase with the matrix (separation of the composition in its packaging). Furthermore, fluorinated oils exhibit the disadvantage of being difficult to formulate, in particular in anhydrous media, thus limiting the range of cosmetic products which can be produced industrially.

Revlon has also envisaged, in the document U.S. Pat. No. 5,837,223, combining a fluorinated Guerbet ester with a siloxysilicate resin and volatile solvents, such as cyclic silicones. The presence of siloxysilicate resin also results in uncomfortable matt films. Furthermore, the presence of fluorinated oil makes it difficult to formulate the cosmetic products. In patent U.S. Pat. No. 5,849,275, Revlon has also envisaged combining a fluorinated polymer with volatile solvents, such as cyclic silicones. Here again, the presence of fluorinated compounds makes it difficult to formulate the cosmetic products.

Application EP-A-775 483 from L'Oréal discloses liquid lipstick compositions comprising a continuous aqueous medium including a polymer dispersion capable of forming a continuous, glossy and "transfer-free" film on the lips. Unfortunately, these compositions result in a film on the lips, continually in movement, which is uncomfortable and which confers a feeling of tautness. In addition, it is very difficult to introduce pigments into these compositions without destabilizing them.

Application EP-A-0 749 746 from L'Oréal discloses lipstick compositions comprising a dispersion of polymer particles which are stabilized at the surface by a polymeric stabilizing agent. These compositions have the disadvantage of only being able to comprise a low proportion of polar oils known in conventional compositions for contributing gloss to the deposited film. In particular, the presence of a high proportion of polar oils (at least 5%) lead to flocculation of the particles and thus to instability of the compositions over time.

The need thus remains for a composition which does not exhibit the above disadvantages and which has in particular notable "transfer-free" properties, even during pronounced pressure or rubbing, great hold over time and a glossy appearance and which does not dry out the skin or the lips to which it is applied, either during application or over time. Furthermore, this composition is stable over time and easy to manufacture and the introduction of pigments is easily carried out.

A specific subject matter of the invention is a composition for caring for and/or making up and/or treating the skin and/or lips of the face and/or the superficial body growths which makes it possible to convey the abovementioned disadvantages.

The Applicant has found, surprisingly, that the use of specific polymers in combination with one or more volatile solvents makes it possible to produce a stick, the application of which to the lips results in a film which has notable cosmetic properties. In particular, the film is glossy, flexible, comfortable and "transfer-free". Furthermore, the composition is stable over time and does not exude at ambient temperature.

The term "stable" is understood to mean a composition which does not exude at ambient temperature for at least 2 months, indeed even up to 9 months.

The invention applies not only to products for making up the lips, such as lipsticks, lip glosses and lip pencils, but also to products for caring for and/or treating the skin, including the scalp, face or body, and the lips, such as products, in particular stick products, for the anti-sun protection of the skin of the face or lips, to products for making up the skin, both of the human face and of the human body, such as foundations, optionally cast as a stick or in a dish, concealers, eyeshadows and temporary tattooing products, to body hygiene products, such as deodorants, in particular stick deodorants, shampoos and conditioners, to products for making up the eyes, such as eyeliners, pencils and mascaras, more especially in the cake form, and to products for caring for keratinous fibres, such as the hair and eyebrows.

One subject matter of the invention is a structured composition comprising at least one liquid fatty phase comprising at least one volatile solvent, the liquid fatty phase being structured by at least one polymer with a weight-average molecular mass of less than or equal to 100 000 comprising a) a polymer backbone having hydrocarbonaceous repeat units provided with at least one heteroatom and b) at least one optionally functionalized pendant and/or end fatty chain having from 6 to 120 carbon atoms which is bonded to these hydrocarbonaceous repeat units, the liquid fatty phase and the polymer forming a physiologically acceptable medium.

The term "at least one fatty chain" is understood to mean one or more pendant fatty chains, one or more end fatty chains, or a combination of these chains. The composition of the invention advantageously does not comprise silicone resin with siloxysilicate units or trimethylated silica, in order to retain the comfort properties of the composition.

The composition of the invention can be provided in the form of a paste, a solid or a more or less viscous cream. It can be an oil-in-water or water-in-oil emulsion or a stiff or soft anhydrous gel. It is provided in particular in the form cast as a stick or in a dish and more especially in the form of a stiff anhydrous gel, in particular an anhydrous stick. More especially, it is provided in the form of a stiff gel which is translucent or transparent, the liquid fatty phase forming the continuous phase.

The gelling of the oil can be adjusted according to the nature of the heteroatom-comprising polymer used and can be such that a stiff structure is obtained in the form of a wand or a stick. These wands, when they are colored, make it possible, after application, to obtain a layer which is glossy and homogeneous in color, which does not transfer, in particular onto a substrate brought into contact with the film, after evaporation of the volatile solvent, and which has good hold, in particular of the color, over time.

The structuring polymer of the composition of the invention is a solid which is nondeformable at ambient temperature (25° C.) and atmospheric pressure (760 mm of Hg). It is capable of structuring the composition without opacifying it.

The term "functionalized chains" is understood to mean, within the meaning of the invention, an alkyl chain comprising one or more functional or reactive groups chosen in particular from the hydroxyl, ether, oxyalkylene or polyoxyalkylene, carboxylic acid, amine, halogen, ester, siloxane or polysiloxane groups, the halogen groups including fluorinated or perfluorinated groups. In addition, the hydrogen atoms of one or more fatty chains can be at least partially substituted by fluorine atoms.

The term "polymer" is understood to mean, within the meaning of the invention, a compound having at least 2 identical repeat units, preferably three identical units.

The term "hydrocarbonaceous repeat unit" is understood to mean, within the meaning of the invention, a unit comprising from 2 to 80 carbon atoms and preferably from 2 to 60 carbon atoms, carrying hydrogen atoms and optionally oxygen atoms, which can be linear, branched or cyclic and saturated or unsaturated. These units each additionally comprise from one to several non-pendant heteroatoms which are found in the polymer backbone. These heteroatoms are chosen from nitrogen, sulfur or phosphorus atoms and their combinations and better still nitrogen atoms, optionally in combination with one or more oxygen atoms. Preferably, the units comprise at least one nitrogen atom, in particular a non-pendant nitrogen atom. In addition, the units advantageously comprise a carbonyl group.

These heteroatom-comprising units are in particular amide units, forming a backbone of the polyamide type, or carbamate and/or urea units, forming a polyurethane, polyurea and/or polyurea-urethane backbone. These units are preferably amide units. The pendant chains are advantageously bonded directly to at least one of the heteroatoms of the polymer backbone. When the repeat units are urea units, the end chains are not bonded to the polyurea backbone via a urethane unit.

The polymer can comprise silicone units or oxyalkylenated units between the hydrocarbonaceous units.

In addition, the polymer of the composition of the invention advantageously comprises from 40 to 98% of fatty chains with respect to the total number of heteroatom-comprising units and of fatty chains and better still from 50 to 95%. The nature and the proportion of the heteroatom-comprising units depends on the nature of the liquid fatty phase and is in particular similar to the nature of the fatty phase. Thus, the more the heteroatom-comprising units increase in polarity and in proportion in the polymer, which corresponds to the presence of several heteroatoms, the greater the affinity of the polymer for polar oils. On the other hand, the more the heteroatom-comprising units decrease in polarity, indeed even become nonpolar, or in proportion, the greater the affinity of the polymer for nonpolar oils.

The fatty chains are bonded to the polymer backbone via a bonding group which can be a single bond, a urea, urethane, ester, ether, amine, thioether, thioester, thiourea or thiourethane group, or their combinations. The bonding group is preferably the ester group.

Another subject matter of the invention is a structured composition comprising at least one liquid fatty phase comprising at least one volatile solvent, the liquid fatty phase being structured by at least one polyamide with a weight-average molecular mass of less or equal to 100 000 comprising a) a polymer backbone having amide repeat units and b) optionally at least one optionally functionalized pendant and/or end fatty chain having from 6 to 120 carbon atoms which is bonded to these amide units, the liquid fatty phase and the polymer forming a physiologically acceptable medium.

Preferably, the pendant fatty chains are bonded to at least one of the nitrogen atoms of the amide units.

In particular, the fatty chains of this polyamide represent from 40 to 98% of the total number of amide units and of fatty chains and better still from 50 to 95%.

Mention may be made, as preferred structuring polymers which can be used in the invention, of polyamides branched by pendant fatty chains and/or end fatty chains having from 6 to 120 carbon atoms, in particular from 12 to 120 carbon atoms and better still from 12 to 68 carbon atoms, the end fatty chains being bonded to the polymer backbone via ester groups.

These polymers are preferably polymers resulting from a polycondensation between a dicarboxylic acid comprising at least 32 carbon atoms (having in particular from 32 to 44 carbon atoms) with a diamine having at least 2 carbon atoms (having in particular from 2 to 36 carbon atoms). The diacid is preferably a dimer of a fatty acid having at least 16 carbon atoms, such as oleic, linoleic or linolenic acid. The diamine is preferably ethylenediamine, hexylenediamine, hexamethylenediamine, phenylenediamine or ethylenetriamine and better still ethylenediamine. For polymers comprising one or 2 end carboxylic acid groups, it is advantageous to esterify them with a monoalcohol having at least 4 carbon atoms, preferably from 10 to 36 carbon atoms, better still from 12 to 24 and ever better still from 16 to 24, for example comprising 18 carbon atoms.

These polymers are more particularly those disclosed in the document U.S. Pat. No. 5,783,657 of Union Camp. Each of these polymers satisfies in particular the following formula (I):

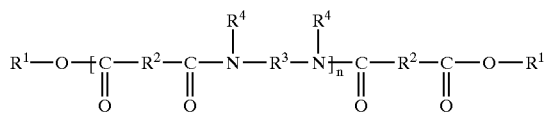

(I)

in which n denotes a whole number of amide units, such that the number of ester groups represents from 10% to 50% of the total number of ester and amide groups; $R^1$ is, in each case, independently an alkyl or alkenyl group having at least 4 carbon atoms and in particular from 4 to 24 carbon atoms; $R^2$ independently represents, in each case, a $C_4$ to $C_{42}$ hydrocarbonaceous group, provided that 50% of the $R^2$ groups represent a $C_{30}$ to $C_{42}$ hydrocarbonaceous group; $R^3$ independently represents, in each case, an organic group provided with at least 2 carbon atoms, with hydrogen atoms and optionally with one or more oxygen or nitrogen atoms; and $R^4$ independently represents, in each case, a hydrogen atom, a $C_1$ to $C_{10}$ alkyl group or a direct bond to $R^3$ or to another $R^4$, so that the nitrogen atom to which both $R^3$ and $R^4$ are bonded forms part of a heterocyclic structure defined by $R^4$—N—$R^3$, with at least 50% of the $R^4$ groups representing a hydrogen atom.

In the specific case of the formula (I), the optionally functionalized end fatty chains within the meaning of the invention are end chains bonded to the final heteroatom, in this instance nitrogen, of a polyamide backbone.

In particular, the ester groups of the formula (I), which form part of the end and/or pendant fatty chains within the meaning of the invention, represent from 15 to 40% of the total number of ester and amide groups and better still from 20 to 35%. Furthermore, n advantageously represents an integer ranging from 1 to 5 and better still from 3 to 5. Preferably, $R^1$ is a $C_{12}$ to $C_{22}$ alkyl group and preferably a $C_{16}$ to $C_{22}$ alkyl group. Advantageously, $R^2$ can be a $C_{10}$ to $C_{42}$ hydrocarbonaceous (alkylene) group. Preferably, 50% at least and better still 75% of the $R^2$ groups are groups having from 30 to 42 carbon atoms. The other $R^2$ groups are $C_4$ to $C_{19}$ and even $C_4$ to $C_{12}$ hydrogenated groups. Preferably, $R^3$ represents a $C_2$ to $C_{36}$ hydrocarbonaceous group or a polyoxyalkylenated group and $R^4$ represents a hydrogen atom. Preferably, $R^3$ represents a $C_2$ to $C_{12}$ hydrocarbonaceous group.

The hydrocarbonaceous groups can be linear, cyclic or branched and saturated or unsaturated groups. Furthermore, the alkyl and alkylene groups can be linear or branched and saturated or unsaturated groups.

Advantageously, the polymer of the composition of the invention comprises a weight-average molecular mass ranging [lacuna] 1 000 to 30 000, preferably ranging from 2 000 to 20 000 and better still from 2 000 to 10 000.

According to the invention, the structuring of the liquid fatty phase is obtained using one or more polymers of formula (I). The polymers of formula (I) are generally provided in the form of blends of polymers, it being possible for these blends additionally to comprise a synthetic product (corresponding to a compound of formula (I) with n having the value 0), that is to say a diester.

Mention may be made, by way of examples of structuring polymers which can be used in the composition according to the invention, of the commercial products sold by Bush Boake Allen under the names Uniclear 80 and Uniclear 100. They are sold respectively in the form of an 80% (as active material) gel in a mineral oil and a 100% (as active material) gel. They have a softening point of 88 to 94° C. These commercial products are a blend of copolymer of a $C_{36}$ diacid condensed with ethylene-diamine, with an average molecular mass of approximately 6 000.

The end ester groups result from the esterification of the remaining acid endings with cetyl alcohol, stearyl alcohol or their mixtures (also known as cetearyl alcohol).

Mention may also be made, as structuring polymer which can be used in the invention, of polyamide resins resulting from the condensation of an aliphatic dicarboxylic acid and of a diamine (including compounds having more than 2 carbonyl groups and 2 amine groups), the carbonyl and amine groups of adjacent individual units being condensed via an amide bond. These polyamide resins are in particular those sold under the trade name Versamid® by the companies General Mills Inc. and Henkel Corp. (Versamid 930, 744 or 1655) or by Olin Mathieson Chemical Corp. under the trade name Onamid®, in particular Onamid S or C. These resins have a weight-average molecular mass ranging from 6 000 to 9 000. For further information on these polyamides, reference may be made to the documents U.S.

Pat. No. 3,645,705 and U.S. Pat. No. 3,148,125. More especially, Versamid® 930 or 744 is used.

It is also possible useful the polyamides sold by Union Camp Corp. under the references Uni-Rez (2658, 2931, 2970, 2621, 2613, 2624, 2665, 1554, 2623, 2662) and the product sold under the reference Macromelt 6212 by Henkel. For further information on these polyamides, reference may be made to document U.S. Pat. No. 5,500,209.

The structuring polymers of the composition of the invention advantageously have a softening temperature of greater than 65° C. and in particular of greater than 70° C. which can range up to 190° C. It preferably exhibits a softening temperature ranging from 80 to 130° C. and better still from 80 to 105° C. These polymers are in particular nonwaxy and/or noncrystalline polymers. This softening temperature is lower than that of known structuring polymers, which facilitates the processing of the polymers which are a subject matter of the invention and limits the decomposition of the liquid fatty phase.

The polymers comprising fatty chain(s) which are a subject matter of the invention exhibit, because of their fatty chain, good solubility in oils (namely water-immiscible liquid compounds) and thus result in macroscopically homogeneous compositions, even with a high level (at least 25%) of polymer, in contrast to polymers without a fatty chain.

The polymer is advantageously used in combination with at least one amphiphilic compound which is liquid and nonvolatile at ambient temperature nd which has a hydrophilic/lipophilic balance (HLB) value of less than 12 and in particular ranging from 1 to 8 and preferably from 1 to 5. According to the invention, one or more amphiphilic compounds can be used. The purpose of these amphiphilic compounds is to strengthen the structuring properties of the heteroatom-comprising polymer, to facilitate the processing of the polymer and to improve the ability to be deposited of the stick.

According to the invention, the composition can have a hardness ranging from 20 to 800 g and better still from 20 to 900 g, in particular from 20 to 600 g and, for example, from 150 to 450 g. This hardness can be measured according to a method of penetration of a probe into said composition and in particular using a texture analyzer (for example, TA-XT2i from Rhéo) equipped with an ebonite cylinder with a height of 25 mm and a diameter of 8 mm. The hardness measurement is carried out at 20° C. at the center of 5 samples of said composition. The cylinder is introduced into each composition sample at a prerate of 2 mm/s, then at a rate of 0.5 mm/s and finally at a postrate of 2 mm/s, the total displacement being 1 mm. The value recorded of the hardness is that of the maximum peak. The measurement error is ±50 g.

The hardness can also be measured by the "cheesewire" method, which consists in cutting a stick of lipstick with a width of 8.1 mm and in measuring the hardness at 20° C., by means of a DFGHS 2 dynamometer from Indelco-Chatillon moving at a rate of 100 mm/minute. It is expressed as the shear force (expressed in grams) necessary to cut a stick under these conditions. According to this method, the hardness of a stick composition according to the invention ranges from 30 to 150 g, preferably from 30 to 120 g and, for example, from 30 to 50 g.

The hardness of the composition according to the invention is such that the composition is self-supporting supporting and can easily disintegrate to form a satisfactory layer on the skin and/or lips and/or superficial body growths. In addition, with this hardness, the composition of the invention possesses good impact strength.

According to the invention, the composition in the stick form has the behavior of a deformable and flexible elastic solid, conferring, on application, a notable elastic softness. The stick compositions of the prior art do not have this property of elasticity and of flexibility.

The amphiphilic compound or compounds which can be used in the composition of the invention comprise a lipophilic part bonded to a polar part, the lipophilic part comprising a carbonaceous chain having at least 8 carbon atoms, in particular from 18 to 32 carbon atoms and better still from 18 to 28 carbon atoms. The polar part of this or these amphiphilic compound or compounds is preferably the residue of a compound chosen from alcohols and polyols having from 1 to 12 hydroxyl groups or polyoxyalkylenes comprising at least 2 oxyalkylene units and having from 0 to 20 oxypropylene units and/or from 0 to 20 oxyethylene units. In particular, the amphiphilic compound is an ester chosen from hydroxystearates, oleates or isostearates of glycerol, of sorbitan or of methylglucose or alternatively branched $C_{12}$ to $C_{26}$ fatty alcohols, such as octyldodecanol, and their mixtures. Preference is given, among these esters, to monoesters and mixtures of mono- and diesters.

The level of amphiphilic compound and that of the heteroatom-comprising polymer are chosen according to the gel hardness desired and according to the specific application envisaged. The respective amounts of polymer and amphiphilic compound must be such that they make it possible to obtain a disintegrable stick. In practice, the amount of polymer represents from 0.5 to 80% of the total weight of the composition and better still from 5 to 40%. In practice, the amount of amphiphilic compound represents from 0.1% to 35% of the total weight of the composition and better still from 1% to 15%, if it is present.

The liquid fatty phase of the composition advantageously comprises more than 30% and better still more than 40% of liquid oil(s), having an affinity with the heteroatom-comprising units (similar chemical structure) and better still from S0 to 100%. In particular, the liquid fatty phase structured by a backbone of polymeric type comprises a majority amount, namely greater than 30% and better still than 40% of the total weight of the liquid fatty phase and better still from 50 to 100%, of nonpolar liquid oil or mixture of nonpolar liquid oils and more especially of hydrocarbonaceous oil(s).

The term "hydrocarbonaceous oil" is understood to mean, within the meaning of the invention, oils predominantly comprising carbon atoms and nitrogen atoms, these oils optionally comprising an ester, ether, acid or alcohol group.

For a liquid fatty phase structured by a polymer comprising a partly silicone backbone, this fatty phase preferably comprises more than 30% and better still more than 40% of the total weight of the liquid fatty phase and better still from 50 to 100% of liquid silicone oil or mixture of liquid silicone oils with respect to the total weight of the liquid fatty phase.

For a liquid fatty phase structured by a nonpolar polymer of the hydrocarbonaceous type, this fatty phase advantageously comprises more than 30% and better still more than 40% by weight and better still from 50 to 100% of nonpolar liquid oil or a mixture of nonpolar liquid oils, in particular hydrocarbonaceous oils, with respect to the total weight of the liquid fatty phase.

In particular, the polar oils of the invention are:
hydrocarbonaceous vegetable oils with a high content of triglycerides composed of esters of fatty acids and of glycerol, the fatty acids of which can have varied $C_4$ to $C_{24}$ chain lengths, it being possible for these chains to be linear or branched and saturated or unsaturated;

these oils are in particular wheat germ, maize, sunflower, karite, castor, sweet almond, macadamia, apricot, soybean, cottonseed, alfalfa, poppy, pumpkinseed, sesame, cucumber, rapeseed, avocado, hazelnut, grape seed, blackcurrant seed, evening primrose, millet, barley, quinoa, olive, rye, safflower, candlenut, passionflower or musk rose oils; or triglycerides of caprylic/capric acids, such as those sold by Stearineries Dubois or those sold under the names Miglyol 810, 812 and 818 by Dynamit Nobel;

synthetic oils or synthetic esters of formula $R_5COOR_6$, in which $R_5$ represents the residue of a linear or branched fatty acid comprising from 1 to 40 carbon atoms and $R_6$ represents a hydrocarbonaceous chain, in particular a branched hydrocarbonaceous chain, comprising from 1 to 40 carbon atoms, provided that $R_5+R_6$ is >10, such as, for example, purcellin oil (cetearyl octanoate), isononyl isononanoate, $C_{12}$ to $C_{15}$ alkyl benzoate, isopropyl myristate, 2-ethylhexyl palmitate, isostearate isostearate, or octanoates, decanoates or ricinoleates alcohols or polyalcohols; hydroxylated esters, such as isostearyl lactate or diisostearyl malate; and pentaerythritol esters;

synthetic ethers having from 10 to 40 carbon atoms;

$C_8$ to $C_{26}$ fatty alcohols, such as oleyl alcohol;

$C_8$ to $C_{26}$ fatty acids, such as oleic acid;

their mixtures.

The nonpolar oils according to the invention are in particular silicone oils, such as volatile or nonvolatile and linear or cyclic polydimethylsiloxanes (PDMS) which are liquid at ambient temperature; polydimethylsiloxanes comprising alkyl, alkoxy or phenyl groups which are pendant and/or at the silicone chain end, which groups have from 2 to 24 carbon atoms; phenylated silicones, such as phenyl trimethicones, phenyl dimethicones, phenyltrimethylsiloxydiphenyl-siloxanes, diphenyl dimethicones, diphenylmethyl-diphenyltrisiloxanes or (2-phenylethyl)trimethyl-siloxysilicates; linear or branched hydrocarbons of synthetic or mineral origin, such as volatile or nonvolatile liquid paraffins and its derivatives, liquid petrolatum, liquid lanolin, polydecenes, hydrogenated polyisobutene, such as parleam, or squalane; and their mixtures. Preferably, the structured oils and more especially those structured by polyamides and in particular those of formulae (I) or polyurethanes or polyureas or polyureaurethanes are nonpolar oils and more especially an oil or a mixture of oils of the hydrocarbonaceous type of mineral or synthetic origin chosen in particular from hydrocarbons, in particular alkanes, such as parleam oil, isoparaffins, such as isododecane and squalane, and their mixtures. These oils are advantageously used in combination with one or more phenylated silicone oils.

The liquid fatty phase preferably comprises at least one nonvolatile oil chosen in particular from hydrocarbonaceous oils of mineral, vegetable or synthetic origin, synthetic esters or ethers, silicone oils and their mixtures.

The total liquid fatty phase represents, in practice, from 3 to 99.5% and in particular from 5 to 99.5% of the total weight of the composition, preferably from 20 to 75%.

The liquid fatty phase of the composition according to the invention additionally comprises at least one volatile solvent, namely one or more volatile solvents.

The term "volatile solvent" is understood to mean, within the meaning of the invention, any nonaqueous medium capable of evaporating on contact with the skin or lips in less than one hour at ambient temperature and atmospheric pressure. The volatile solvent or solvents of the invention are organic solvents and in particular volatile cosmetic oils which are liquid at ambient temperature and which have a nonzero vapor pressure, at ambient temperature and atmospheric pressure, ranging in particular from $10^{-3}$ to 300 mm of Hg (0.13 Pa to 40 000 Ps) and preferably greater than 0.03 mm of Hg (3.9 Pa).

The volatile solvents of the invention are preferably cosmetic oils chosen from oils which do not have a flashpoint, oils which have a flashpoint ranging from 40° C. to 100° C., and their mixtures, for the purpose of facilitating their processing. In addition, they advantageously exhibit a boiling point at atmospheric pressure of less than 220° C. and better still of less than 210° C., in particular ranging from 110 to 210° C.

According to the invention, these volatile solvents facilitate in particular the application of the composition to the skin, lips or superficial body growths. These solvents can be hydrocarbonaceous solvents, silicone solvents optionally comprising pendant alkyl or alkoxy groups or alkyl or alkoxy groups at the silicone chain end, or a mixture of these solvents. Preferably, these solvents are not monoalcohols comprising at least 7 carbon atoms.

Mention may be made, as volatile solvent which can be used in the invention, of linear or cyclic silicone oils having a viscosity at ambient temperature of less than 8 cSt and having in particular from 2 to 7 silicon atoms, these silicones optionally comprising alkyl or alkoxy groups having from 1 to 10 carbon atoms. Mention may in particular be made, as volatile silicone oils which can be used in the invention, of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and their mixtures.

Mention may be made, as other volatile solvent which can be used in the invention, of volatile hydrocarbonaceous oils having from 8 to 16 carbon atoms and their mixtures and in particular branched $C_8$–$C_{16}$ alkanes, such as $C_8$–$C_{16}$ and in particular $C_8$–$C_{13}$ isoalkanes (also known as isoparaffins), isodecane, isohexadecane and, for example, the oils sold under the trade names of Isopars L, E, H or G or of Permetyls, branched $C_8$–$C_{16}$ esters, such as isohexyl neopentanoate, and their mixtures. The volatile solvent is preferably chosen from volatile hydrocarbonacecous oils having from 8 to 16 carbon atoms and their mixtures, with the exception of Isopar M.

Volatile fluorinated solvents can also be used.

Use is preferably made of isododecane (Permetyls 99 A), $C_8$–$C_{16}$ isoparaffins (Isopars L, E and H), and their mixtures, optionally in combination with decamethyltetrasiloxane or with cyclopentasiloxane.

These volatile oils represent in particular a level by mass of 3 to 99.5% with respect to the total weight of the composition and in particular of 5 to 97.5%, preferably of 10 to 75% and better still of 15 to 45%. Generally, the amount of volatile solvent is used in an amount sufficient to produce transfer-free properties. This amount will be adjusted by a person skilled in the art according to the desired intensity of the transfer-free properties.

The composition of the invention can additionally comprise any additive conventionally used in the field under consideration chosen in particular from coloring materials, antioxidants, essential oils, preservatives, fragrances, fillers, waxes, products which are pasty at ambient temperature, neutralizing agents, fat-soluble polymers or polymers which are dispersible in the medium, cosmetic or dermatological active principles having a biological effect on the skin, such as, for example, emollients, moisturizers, vitamins or essential fatty acids, sunscreen agents, dispersants, such as poly (12-hydroxystearic acid), and their mixtures. These additives can be present in the composition in a proportion of 0 to 20% (in particular of 0.01 to 20%) of the total weight of the composition and better still of 0.01 to 10%. The composition advantageously comprises at least one cosmetic or dermatological active principle having a biological effect.

The composition of the invention can additionally comprise, as additive, an aqueous phase comprising water, optionally thickened or gelled by a thickener or gelling agent for the aqueous phase, and optionally water-miscible compounds.

Of course, a person skilled in the art will take care to choose the possible additional additives and/or their amounts so that the advantageous properties of the composition according to the invention are not, or not substantially, detrimentally affected by the envisaged addition.

The composition according to the invention can be provided in the form of a dyed dermatological composition or composition for caring for keratinous substances, such as the skin, lips and/or superficial body growths, in the form of an antisun protection or body hygiene composition, in particular in the form of a deodorant or make-up-removing product in the stick form. It can be used in particular as care base for the skin, superficial body growths or lips (lip balms, protecting the lips from the cold and/or sun and/or wind, or care cream for the skin, nails or hair).

The composition of the invention can also be provided in the form of a product, in particular a colored product, for making up the skin, in particular a foundation, optionally exhibiting care or treatment properties, a blusher, a face powder, an eyeshadow, a concealer, an eyeliner or a product for making up the body; of a product for making up the lips, such as a lipstick, optionally exhibiting care or treatment properties; or of a product for making up the superficial body growths, such as the nails, the eyelashes, in particular in the form of a mascara cake, the eyebrows and the hair, in particular in the form of a pencil. The composition of the invention is advantageously a makeup product.

Of course, the composition of the invention must be cosmetically or dermatologically acceptable, namely must comprise a nontoxic physiologically acceptable medium capable of being applied to the skin, superficial body growths or lips of human beings. The term "cosmetically acceptable" is understood to mean, within the meaning of the invention, a composition with a pleasant appearance, smell, taste and feel.

The composition advantageously comprises at least one cosmetic active principle and/or one dermatological active principle and/or at least one coloring material. By virtue of the combination of at least one volatile solvent, as defined above, and of at least one polymer with a weight-average molecular mass ranging from 1 000 to 30 000, as defined above, the active principles and the coloring materials present in the composition are trapped, making it possible to maintain them in the place where they have been applied, namely the lips, skin or superficial body growths, such as keratinous fibers, after evaporation of the volatile solvent or solvents, and to limit their transfer to or redeposition on a substrate other than that to which they were applied.

The coloring material according to the invention can be chosen from lipophilic dyes, hydro-philic dyes, pigments and pearlescent agents commonly used in cosmetic or dermatological compositions, and their mixtures. This coloring material is generally present in a proportion of 0.01 to 50% of the total weight of the composition, preferably of 5 to 30%, if it is present, and better still of 8 to 20%.

The fat-soluble dyes are, for example, Sudan red, DC Red 17, DC Green 6, β-carotene, soybean oil, Sudan brown, DC Yellow 11, DC Violet 2, DC Orange 5, quinoline yellow or annalto. They can represent from 0.1 to 20% of the weight of the composition and better still from 0.1 to 6%.

The pigments can be white or colored, inorganic and/or organic and coated or uncoated. Mention may be made, among inorganic pigments, of titanium or zinc dioxide, optionally treated at the surface, zirconium or cerium oxides, iron or chromium oxides, manganese violet, ultramarine blue, chromium hydrate and ferric blue. Mention may be made, among organic pigments, of carbon black, pigments of D & C type and lakes based on cochineal carmine or on barium, strontium, calcium or aluminum. The pigments can represent from 0.1 to 50% and better still from 2 to 30% of the total weight of the composition, if they are present.

The pearlescent pigments can be chosen from white pearlescent pigments, such as mica covered with titanium or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride. They can represent from 0.1 to 20% of the total weight of the composition and better still from 0.1 to 15%, if they are present.

The composition can optionally comprise one or more waxes for improving the structuring in the stick form, although this stiff form can be obtained in the absence of wax. A wax, within the meaning of the present invention, is a lipophilic fatty compound which is solid at ambient temperature (25° C.), which exhibits a reversible solid/liquid state change, which has a melting point of greater than 45° C. and better still than 55° C. which can range up to 200° C., and which exhibits, in the solid state, an anisotropic crystalline organization. The size of the crystals is such that the crystals diffract and/or scatter light, conferring a cloudy and more or less opaque appearance on the composition. By bringing the wax to its melting point, it is possible to render it miscible with the oils and to form a microscopically homogeneous mixture but, by bringing the temperature of the mixture back to ambient temperature, recrystallization of the wax in the oils of the mixture is obtained. It is this recrystallization in the mixture which is responsible for the decrease in the gloss of said mixture.

Consequently, the composition advantageously comprises little or no wax and in particular less than 5% of wax.

The waxes, within the meaning of the application, are those generally used in the cosmetic and dermatological fields; they are in particular of natural origin, such as beeswax, carnauba, candelilla, ouricury, Japan, cork fiber or sugar cane wax, paraffin or lignite waxes, microcrystalline waxes, lanolin wax, montan wax, ozokerites or hydrogenated oils, such as hydrogenated jojoba oil, but also of synthetic origin, such as polyethylene waxes resulting from the polymerization of ethylene, the waxes obtained by the Fischer-Tropsch synthesis, fatty acid esters and glycerides which are solid at 45° C., or silicone waxes, such as alkyl, alkoxy and/or esters of poly(di)methyl-siloxane, which are solid at 45° C.

The temperature values are in particular those of the known "Dynamic Scanning Calorimetry" method.

Advantageously, the composition of the invention additionally comprises at least one fat-soluble polymer or polymer which is dispersible in the medium exhibiting in particular an average molecular weight of 500 to 1 000 000 and better still of 5 000 to 15 000. This or these fat-soluble polymer or polymers contribute in particular to increasing the viscosity and/or to improving the hold of the film. These fat-soluble polymers advantageously exhibit a softening temperature at most equal to 30° C.

Mention may be made, as examples of fat-soluble polymers which can be used in the invention, of: polyalkylenes, in particular polybutene, poly(meth)acrylates, alkylcelluloses with a saturated or unsaturated and linear or branched $C_1$ to $C_8$ alkyl radical, such as ethylcellulose and propylcellulose, silicone polymers which are compatible with the fatty phase, vinylpyrrolidone (VP) copolymers and their mixtures.

Use is preferably made of vinylpyrrolidone copolymers, $C_2$ to $C_{30}$ and better still $C_3$ to $C_{22}$ alkene copolymers, and their combinations. Mention may be made, as examples of VP copolymer which can be used in the invention, of the VP/vinyl acetate, VP/ethyl methacrylate, VP/ethyl methacrylate/methacrylic acid, VP/eicosene, VP/hexadecene, VP/triacontene, VP/styrene or VP/acrylic acid/lauryl methacrylate copolymer or butylated polyvinylpyrrolidone (PVP).

Preferably, not only for the properties of hold but also of feel and of consistency of the film, use is made of the PVP/hexadecene copolymer having an average molecular weight of 7 000 to 7 500 or the PVP/eicosene [lacuna] having an average molecular weight of 8 000 to 9 000.

The fat-soluble or dispersible polymers of the composition of the invention are advantageously used in an amount of 0.01% to 20% (as active material) of the total weight of the composition and better still of 1% to 10%, if they are present.

In addition, the composition according to the invention advantageously comprises at least one fatty compound which is pasty at ambient temperature. The term "fatty substance which is pasty" is understood to mean, within the meaning of the invention, fatty substances having a melting point ranging from 20 to 55° C., preferably 25 to 45° C., and/or a viscosity at 40° C. ranging from 0.1 to 40 Pa·s (1 to 400 poises), preferably 0.5 to 25 Pa·s, measured with a Contraves TV or Rheomat 80 equipped with a rotor rotating at 60 Hz. A person skilled in the art can choose the rotor which makes it possible to measure the viscosity from the MS-r 3 and MS-r 4 rotors on the basis of his general knowledge, so as to be able to carry out the measurement of the pasty compound tested.

According to the invention, use is made of one or more fatty substances which are pasty. These fatty substances are preferably hydrocarbonaceous compounds, optionally of polymeric type; they can also be chosen from silicone and/or fluorinated compounds; it can also be provided in the form of a mixture of hydrocarbonaceous and/or silicone and/or fluorinated compounds. In the case of a mixture of various fatty substances which are pasty, use is preferably made of predominantly hydrocarbonaceous pasty compounds.

Mention may be made, among pasty compounds capable of being used in the composition according to the invention, of lanolins and lanolin derivatives, such as acetylated lanolins or oxypropylenated lanolins having a viscosity of 18 to 21 Pa·s, preferably 19 to 20.5 Pa·s, and/or a melting point of 30 to 55° C., and their mixtures. Use may also be made of esters of fatty acids or fatty alcohols, in particular those having 20 to 65 carbon atoms (melting point of the order of 20 to 35° C. and/or viscosity at 40° C. ranging from 0.1 to 40 Pa·s), such as triisostearyl or ketyl citrate; arachidyl propionate; poly(vinyl laurate); cholesterol esters, such as triglycerides of vegetable origin, such as hydrogenated vegetable oils, viscous polyesters, such as poly(12-hydroxystearic acid), and their mixtures. Use may be made, as triglycerides of vegetable origin, of derivatives of hydrogenated castor oil, such as "Thixinr" from Rheox.

Mention may also be made of silicone fatty substances which are pasty, such as polydimethyl-siloxanes (PDMS) having pendant chains of the alkyl or alkoxy type having from 8 to 24 carbon atoms and a melting point of from 20–55° C., such as stearyl dimethicones, in particular those sold by Dow Corning under the trade names of DC2503 and DC25514, and their mixtures.

The fatty substance which is pasty or the fatty substances which are pasty can be present in a proportion of 0.1 to 60% by weight with respect to the total weight of the composition, preferably in a proportion of 1–45% by weight and more preferably still in a proportion of 2–30% by weight in the composition, if they are present.

The composition according to the invention can be manufactured by known processes generally used in the cosmetic or dermatological field. It can be manufactured by the process which consists in heating the polymer to at least its softening temperature, in adding thereto the amphiphilic compound or compounds, the coloring materials and additives, and then mixing the combined mixture until a light and transparent solution is obtained. The volatile solvent or solvents is/are then added to the mixture obtained, after lowering the temperature. The homogeneous mixture obtained can then be cast in an appropriate mold, such as a lipstick mold, or directly in packaging items (case or dish, in particular).

A further subject matter of the invention is a lipstick composition as a stick comprising at least one continuous liquid fatty phase comprising at least one volatile solvent, the liquid fatty phase being structured by at least one nonwaxy polymer which confers on the composition the appearance of a deformable and elastic solid with a hardness ranging from 30 to 50 g, in the absence of wax.

This lipstick composition as a stick advantageously comprises an additive chosen from fatty substances which are pasty at ambient temperature or fat-soluble polymers, and their mixtures, as defined above. The nonwaxy polymer is preferably a polymer with a backbone comprising heteroatom-comprising hydro-carbonaceous units as defined above.

A further subject matter of the invention is a cosmetic process for caring for, making up or treating human keratinous substances and in particular the skin, lips and superficial body growths comprising the application to the keratinous substances of the composition, in particular the cosmetic composition, as defined above.

Another subject matter of the invention is the use of a combination of at least one volatile solvent and of at least one polymer with a weight-average molecular mass ranging from 1 000 to 30 000, comprising a) a polymer backbone having hydrocarbon-aceous repeat units provided with at least one hetero-atom and b) optionally at least one optionally functionalized pendant and/or end fatty chain having from 12 to 120 carbon atoms which is bonded to these hydrocarbonaceous units, in a cosmetic composition or for the manufacture of a physiologically acceptable composition, for decreasing the transfer onto and/or the deposition on a substrate of traces of a film of said composition, applied to keratinous substances, brought into contact with said substrate and/or for increasing the hold of said film. In addition, this film is glossy and/or comfortable.

The invention is illustrated in more detail in the following examples. The percentages are given as percentage by mass.

EXAMPLE 1

Lipstick

| Phase A | |
|---|---|
| Uniclear 100 | 18% |
| Castor oil | 7% |
| Hydrogenated isoparaffin | 4% |
| Isononyl isononanoate | 4% |
| Phenyltrimethylsiloxytrisiloxane | 8% |
| Vinylpyrrolidone/1-eicosene copolymer | 2% |
| Phase B | |
| Pigments | 10% |
| Hydrogenated isoparaffin | 5% |
| Liquid lanolin | 5% |
| Poly(12-hydroxystearic acid) | 2% |
| Phase C | |
| Isododecane | 25% |
| Decamethyltetrasiloxane | 10% |

The pigmentary phase (B) is milled using a triple roll mill and is introduced into the oily phase A, heated beforehand to 100° C., until the mixture is completely homogenous. The volatile phase C is subsequently added to the preceding mixture, which has been brought back to 85° C. The combined mixture is left in contact for 10 min and then cast in lipstick molds.

The lipstick obtained deposits a glossy and transfer-free film. This lipstick was considered by those testing to have a hold equal to and transfer-free and nonmigrating property or equivalent and to those of a transfer-free lipstick of the prior art, such as disclosed in Example 1 of document EP-A-847 752, but to be glossier than that of the prior art. This known lipstick contained:

| PDMS (100 cSt) | 8% |
|---|---|
| Hydrogenated polyisobutene | 18% |
| Arachidyl propionate | 7.5% |
| Polyethylene wax | 16.5% |
| Pigments/pearlescent agents | 11% |
| Isododecane | qsp 100% |

EXAMPLE 2

Lipstick

| Phase A | |
|---|---|
| Uniclear 100 | 18% |
| Castor oil | 8% |
| Hydrogenated isoparaffin | 5% |
| Isononyl isononanoate | 5% |
| Phenyltrimethylsiloxytrisiloxane | 8% |
| Vinylpyrrolidone/1-eicosene copolymer | 2% |
| Phase B | |
| Pigments | 10% |
| Hydrogenated isoparaffin | 5% |
| Liquid lanolin | 5% |
| Poly(12-hydroxystearic acid) | 2% |
| Phase C | |
| Isododecane | 27% |
| Decamethyltetrasiloxane | 5% |

The pigmentary phase (B) is milled using a triple roll mill and is introduced into the oily phase A, heated beforehand to 100° C., until the mixture is completely homogenous. The volatile phase C is subsequently added to the preceding mixture, which has been brought back to 85° C. The combined mixture is left in contact for 10 min and then cast in lipstick molds.

The lipstick obtained deposits a glossy and transfer-free film. This lipstick was considered, by a panel of testers, to have a hold equal to and transfer-free and non-migration properties equivalent to those of a transfer-free lipstick of the prior art, in accordance with that of Example 1 of document EP-A-847 752, but to be glossier than that of the prior art.

What is claimed is:

1. A method for making up eyelashes comprising applying to said eyelashes a mascara comprising:

(i) isododecane;

(ii) at least one polymer chosen from ethylenediamine/stearyl dimer tallate copolymer;

(iii) water;

(iv) at least one coloring agent; and (v) at least one preservative.

2. A method for making up eyelashes comprising applying to said eyelashes a mascara comprising:

(i) isododecane:

(ii) at least one polymer chosen from ethylenediamine/stearyl dimer dilinoleate copolymer;

(iii) water;

(iv) at least one coloring agent, and (v) at least one preservative.

* * * * *